United States Patent
Conway et al.

(10) Patent No.: US 8,019,554 B2
(45) Date of Patent: Sep. 13, 2011

(54) PREDICTIVE INDICATOR MODEL

(75) Inventors: Lea Ann Conway, Flemington, NJ (US); David W. Powell, San Juan Capistrano, CA (US); Susanne Manz, Bridgewater, NJ (US); Robert M. Smith, Lake Villa, IL (US); Mizanu Kebede, San Clemente, CA (US)

(73) Assignee: Ethicon, Inc., Norwood, MA (US)

( * ) Notice: Subject to any disclaimer, the term of this patent is extended or adjusted under 35 U.S.C. 154(b) by 727 days.

(21) Appl. No.: 11/093,415

(22) Filed: Mar. 30, 2005

(65) Prior Publication Data

US 2006/0224325 A1 Oct. 5, 2006

(51) Int. Cl.
 *G01N 33/48* (2006.01)
 *G06F 13/10* (2006.01)
(52) U.S. Cl. .......................................... 702/19; 703/21
(58) Field of Classification Search ........................ None
 See application file for complete search history.

(56) References Cited

U.S. PATENT DOCUMENTS

| 6,353,767 | B1 | 3/2002 | Wakeman et al. | |
|---|---|---|---|---|
| 6,741,951 | B2 | 5/2004 | Whaling et al. | |
| 6,757,660 | B2 | 6/2004 | Canada et al. | |
| 2003/0125997 | A1* | 7/2003 | Stoltz | 705/7 |
| 2003/0149499 | A1 | 8/2003 | Kirshenbaum | |
| 2003/0163349 | A1 | 8/2003 | Ho | |
| 2004/0083019 | A1 | 4/2004 | Suzuki et al. | |
| 2004/0117051 | A1 | 6/2004 | Ford | |

OTHER PUBLICATIONS

Justiniano et al. (Six Sigma for Medical Device Design, CRC Press, Nov. 2004, chapters 1-6 and appendix, pp. 1-128).*

* cited by examiner

*Primary Examiner* — Marjorie Moran
*Assistant Examiner* — Larry D Riggs, II
(74) *Attorney, Agent, or Firm* — Nutter McClennen & Fish LLP

(57) ABSTRACT

A predictive indicator tool for predicting the risk of a manufacturing process producing products having defects. Manufacturing sub-processes are identified for the process and s a series of 12 questions is applied to each sub-process. The questions are generated using Six Sigma statistical techniques. The questions are scored and an associated algorithm is applied to produce a quantitative score is indicative of risk. The quantitative risk score is compared to an alert level.

3 Claims, 2 Drawing Sheets

| CATEGORY | QUESTION | SCORE EXPLANATION | DOCUMENT SOURCES |
|---|---|---|---|
| Severity | Question 1- What is the level of patient risk due to potential failure of this product? | 1=Failure has little or no patient impact; 3= failure significance greater than 1 but less than 9; 9=Failure has significant impact on patient (sterility, life sustaining). | Design History File (Design Control Input / Output Matrix, Product Risk Assessment, Clinical Evaluation / Studies), Risk Management File (Risk Assessment), and Classification of Defects |
| Severity | Question 2- What is the level of regulatory risk related to this product or process? | FDA Classifications: 1= class I device, 3= class II device where process does not include labeling functions, 7= class II with labeling, 9= class III. EU Classifications: class I device (Sterile & Non-Sterile), 3= class II a device, 7= class II b dev, 9=class III | Technical File/Design Dossier, the 510K, PMA |
| Design | Question 3 -Are product CTQs identified and linked to VOC? | 1=all utilizing QFD or equivalent, 5=some known through complaint or other history, 9=none or unknown. | Product Specifications/Quality Plan, QFD, Complaint history, DHF |
| Design | Question 4- Is a product risk assessment complete and risk mitigation plan in place? | 1=yes, 5=complete but not all failure modes addressed, 9=no or unknown | Risk Management File, DDSA, FMEA |
| Materials | Question 5-Have CTQs flowed down to component/RM level with control plans in place for each component/RM? | 1=all, 5=some, 9=none | Quality Plan/Raw Material Specifications |
| Measurements | Question 6 - Do sampling plans / control strategies utilize documented statistical rationales? | 1=all, 7=some, 9=none | PE BB Project/Operator Inspection Sheet/Validation/Specific Defect Audit/Incoming Inspection Sampling |
| Methods | Question 7-Does a control plan exist and identify KPIVs and controls for each CTQ? | 1=control plan complete and Y=f(x) relationship documented, 5=some, 9=no | Specifications/Quality Plan/Operator Inspection System |
| Measurements | Question 8 - Is an adequate test method control identified for each CTQ? | 1= GR&R<20, 3= GR&R of 20-30, attribute, compendial or TM validated using other valid TMV technique, 9= GR&R>30 or unknown value or TM does not correlate to the targeted CTQ. | Quality Plan/Test Method Validation Index |
| Machine | Question 9 - What is the critical defect (3 month average) process capability in DPM or Ppk (complete roll-up)? | 1= less than 3.4dpm or Ppk better than 1.5; 3 = Ppk 1.17 to 1.5 or dpm 233 to 3.4; 9 = Ppk less than 1.17 or dpm greater than 233 or unknown or no SPC | DPM Tracking System, Defect Tracking System (DTS) or CAPA System |
| Manpower | Question 10 - Is there an Effective Training Plan defined, followed, and up to date? | 1=yes, 7=some, 9=no | Personnel Training Records, Annual Assessments of Competence, Training Plan |
| Manpower | Question 11 - Are manufacturing methods and other procedures properly executed (# of unintentional process deviations on the last 3 months)? | 1= 0 process deviations, 3= 1-2 process deviations, 9= 3 or more process deviations | Deviation System Records, CAPA System |
| Methods | Question 12 - Is a process FMEA complete and adequate? | 1=yes with acceptable RPNs, 3= complete with unacceptable RPNs, 9=no FMEA | Risk Management File/Design History File, pFMEA |

FIG. 2

PREDICTIVE INDICATOR MODEL

TECHNICAL FIELD

The field of art to which this invention relates is business methods, more specifically, methods of statistically predicting risk in manufacturing processes.

BACKGROUND OF THE INVENTION

Statistical analysis as a way of controlling the quality of the product produced by a manufacturing process is well known in the art. Data is collected and various process parameters are measured for conformance with standards. The conformance of the parameters to a range is typically related to a measure of the quality of the product. Variations of the parameters from the accepted range are indicative of a process that is out of control, possibly resulting in products that do not conform to specifications.

One example of a quality assurance process is the six-sigma process. The six-sigma process is a problem solving methodology using statistical tools. The six-sigma process is utilized by many businesses to solve quality and business problems.

Other examples of quality assurance processes or methods include: inspection and testing, validation, risk management, statistical process control, and pre-control.

Quality assurance is especially critical in the manufacture of medical devices, diagnostics and pharmaceutical products. The use of quality assurance processes for the manufacture of medical devices, diagnostics and pharmaceutical in the United States is mandated by law by the U.S. Food and Drug Administration (FDA). The FDA has promulgated Good Manufacturing Practice regulations (GMPs) that must be strictly complied with. The GMPs cover all aspects of the manufacture of regulated products, including controls over design, raw materials, sampling, assembly, testing, storage, sterilization, etc. Given that most FDA-regulated products are mass-produced, it is neither possible nor desirable to quality control test every product prior to release. Some products, such as sterile implantable medical devices or injectable pharmaceuticals, cannot be tested for conformance to specifications after manufacture without destroying or adversely affecting the product. Accordingly, it is important to build quality into a product by the use of various quality assurance processes, as required by the GMPs and other quality assurance methodologies.

Although the GMPs and statistical control systems provide for quality products, there is also a need for e effective predictive systems so that potential risks can be identified and resolved to prevent product that does not conform to specifications from being released, even though the processes conform to GMPs. It can be appreciated that in FDA-regulated industries, it is critical to patient safety and welfare that devices and pharmaceuticals strictly conform to specifications so that they are safe and effective for their intended use. Many medical devices are implanted in patients, and if defective, cannot be readily retrieved and/or replaced without threatening the life or safety of the patients. Failure of critical medical devices may be catastrophic resulting in serious injury to the patient. Similarly, defective pharmaceutical products can be harmful to patients, e.g., non-sterile injectables, dosage strength that is too high or too low, misbranded or contaminated pharmaceuticals, etc. When defects in FDA-regulated products that have been released are discovered, either through reports from the field or otherwise, it is necessary to recall products from distribution to prevent injuries to patients. This entails considerable cost, and is often accompanied by adverse publicity, even though the manufacturer has used its best efforts to manufacture the products in conformance with GMPs. And, as previously mentioned, defective medical devices that have been implanted in patients may not be retrievable.

In the quality systems, processes and methods of the prior art, multiple layers of protection in these systems and methods exist to prevent products containing defects from reaching the customer and consumer. However, when gaps in these systems and methods align (i.e., a perfect storm scenario), a situation may be created wherein a potential risk of product nonconformance is created. None of the previously mentioned statistical quality methods, processes and systems provides the user with a reliable prediction of potential risk in the manufacturing processes utilized to produce products. There is a need for a proactive method of identifying risk in manufacturing processes in order to prioritize and subsequently resource quality improvement efforts in order to provide an additional layer of assurance that product is free from defects. There is a need in this art for novel methods of predicting defects in products based upon an analysis of design, regulatory risk, and the manufacturing process variables associated with these products. Such a method would facilitate a more predictive process of identifying potential risks, thus presenting the opportunity to reduce or eliminate the incidence of manufacturing defects in finished products.

SUMMARY OF THE INVENTION

Accordingly, a method of identifying and prioritizing potential areas of risk in manufacturing processes using a predictive indicator tool is disclosed. The predictive indicator tool method has a series of steps for analyzing and responding to a series of questions regarding a particular product line and it's associated manufacturing process. The initial step is create a process map for the manufacturing process and identify each sub-process. The following 12 questions are evaluated and scored for each sub-process:

1—What is the Level of Patient Risk due to potential failure of this product?
2—What is the Level of Regulatory Risk related to this product or process?
3—Are Product CTQs identified and linked to VOC?
4—Is a Product Risk Assessment complete and risk mitigation plan in place?
5—Have CTQs Flowed Down to Component/Raw Material Level with control plans in place for each component/Raw Material?
6—Do Sampling Plans/Control Strategies utilize documented statistical rationales?
7—Does a Control Plan Exist and identify KPIVs and controls for each CTQ?
8—Is an Adequate Test Method control identified for each CTQ?
9—What is Critical Defect Process Capability (3 month average) in DPM or Ppk (complete roll-up)?
10—Is there an Effective Training Plan defined, followed, and up to date?
11—Are Manufacturing Methods and other procedures properly executed (# of human error deviations)?
12—Is a Process FMEA complete and adequate?

A scoring system is provided for the 12 questions such that the cumulative total will be in the range of 0-100. A particular product line, and its associated manufacturing process or unique manufacturing sub processes, are considered as each question is applied The questions are each scored and an overall score is determined. The score is calculated based upon the application of an algorithm, listed below, that has been derived from a careful analysis of medical device and diagnostic defects produced over a period of time. The higher the score, the more potential risk a process, and it's associated product line, has. The lower the score, the lower potential risk. An alert level is calculated for a manufacturing site or company, which will facilitate ease of prioritization of quality improvement efforts. Processes, which score over the alert level, require formal preventive action plans to correct and/or eliminate the risk. The following algorithm is used to calculate the overall score:

PI=Severity*Detection*Occurrence divided by the maximum score and multiplied by 100, wherein:

Severity=the sum of Questions 1 and 2;
Occurrence=the sum of Questions 3, 4, 5, 7, 9, 10, 11 and 12.
Detection=the sum of Questions 6 and 8

These and other aspects and advantages of the present invention will become more apparent from the following description and accompanying drawings.

BRIEF DESCRIPTION OF THE DRAWINGS

FIG. 2 is an illustration of a predictive indicator tool for a medical device or diagnostic manufacturing process.

DETAILED DESCRIPTION OF THE PREFERRED EMBODIMENTS

Figure 1:
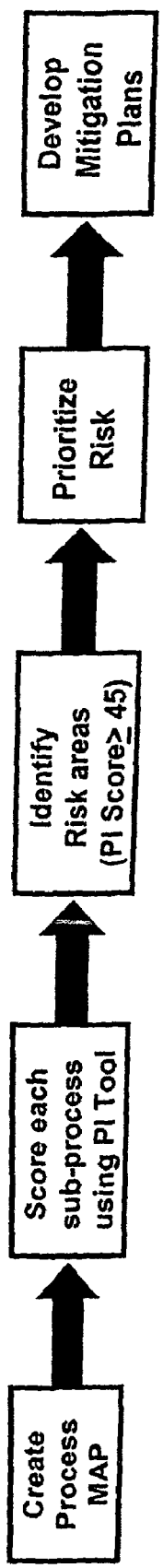
FIG. 1 is a flow diagram of how the predictive indicator tool is utilized or the method of the present invention.

The Predictive Indicator Tool (PI Tool) method of the present invention, is a novel method of predicting areas in manufacturing processes with a higher risk of potential non-conformances based upon answering and scoring questions related to product design, regulatory risk, and the manufacturing process variables associated with the products produced in the process.

The method facilitates a more predictive process than GMPs and statistical control systems of identifying potential risks, thus providing a means to identify and prioritize quality improvement efforts and preventive actions. The purpose of the novel method of the present invention is to identify through scoring processes the potential risk, based upon answering questions related to the product's design, regulatory risk and associated performance of the manufacturing process that produced the product. In this method, the scores are then used to prioritize quality improvement efforts.

The predictive indicator tool was developed using conventional, known Six Sigma statistical tools and techniques. Using these Six Sigma tools and techniques, a series of twelve scored questions was generated to serve as a predictive indicator of risk. The following is a discussion and listing of the conventionally known tools and techniques, including acronyms, which are utilized in the predictive indicator tool of the present invention.

Corrective Action and Preventive Action Metrics (CAPA Metrics) means metrics or categories of defects/nonconformances/quality issues cataloged in a company's CAPA system.

Management Action Plan Items (MAP Items) means a management tool to track corrective and preventive actions associated with resolution of systemic quality issues. It is a component of a management awareness and action review system.

Product Critical to Quality Requirements (CTQs) are those critical quantified requirements for products/services that must be met in order to satisfy customer needs. These are specific requirements translated from broad (unspecific) customer requirements. It is a Six Sigma tool.

Voice of the Customer (VOC) is a Six Sigma term used to describe a process for collecting customer needs and their perceptions of how a specific product or service can meet those needs. It is a Six Sigma tool utilized to decide what products, services, or features to offer.

Process Performance Index (Ppk) is a term used in Six Sigma that is basically used to verify if the sample generated from the process is capable of meeting customer CTQs (requirements). It applies to a specific batch of material and represents the long-term capability of the process.

Process Failure Mode and Effects Analysis (Process FMEA) is a structured approach utilized to identify, estimate, prioritize and evaluate potential risk in a process.

Failure Mode and Effects Analysis (FMEA) is a structured approach that systematically analyzes design or process functions and determined failure modes, their causes and effects. Risk is estimated by rating the severity of failure effects, the likelihood of detecting the cause of the failure and the potential frequency of the failure mode.

Quality Function Deployment (QFD) is also known as "the House of Quality" and ties product and design decisions directly to customer wants and needs, i.e., "The Voice of the Customer". QFD deploys customer input throughout the design, production, marketing and delivery facets of a given product or service.

Gage Repeatability & Reproducibility Study (GR&R) is a study that assesses the accuracy, repeatability and reproducibility of a continuous measurement system. It is used to validate a measurement system to insure that most of the variation is accounted for by physical or actual differences between the units being measured, and that the measurement system has sufficient precision.

Statistical Process Control (SPC) is a method of monitoring, controlling, and ideally, improving a process through statistical analysis. The goal of SPC is to eliminate variances in the process to make it consistent.

Key Process Input Variables (KPIVs) is a six sigma term that indicates the key or important process inputs or factors that drive the key process outputs of a process.

Defects per Million Units (DPM) is a six sigma term that indicates the number of defects in a process, procedure or service for every million units produced.

A flow diagram for the use of the predictive indicator tool of the present invention is illustrated in FIG. 1. The initial step in the process is to create a process map of the manufacturing process by identifying each sub-process or unique step in the overall manufacturing flow. The next step of the process as indicated in FIG. 1 is to score each sub-process using the predictive indicator tool method of the present invention. This is accomplished by asking a series of 12 questions, as indicated below, for each sub process. Next, using the algorithm provided below, a predictive indicator risk score is calculated. If the risk score is equal to or greater than 45, this represents a potential risk. Then, all sub processes having a potential risk are prioritized and mitigation plans developed. Although the alert level as illustrated in FIG. 1 is set at 45, the alert level may vary and is set and calculated as further described herein below.

An example of the predictive indicator tool questions of the present invention is seen in FIG. 2, which illustrates a series of 12 questions utilized to score a manufacturing process for a medical device or diagnostic product in order to determine a cumulative score that will serve as a predictor of risk associated with the manufacturing process used to produce the product. Also listed are exemplary sources which may be used in the evaluation and scoring for each question. The initial step in the predictive indicator tool method of the present invention is to identify the product being evaluated, and then the associated specific sub-processes utilized to manufacture that product, i.e., map out the sub-processes of the manufacturing process. The following is a listing of questions that must be answered and scored for each sub-process.

Referring to FIG. 2, the first question (Question #1) asked is "What is the level of patient risk due to potential failure of this product?". The evaluator scores the risk as follows:
Scoring:
1=Failure has little or no patient impact
3=Failure significance greater than 1 but less than 9
9=Failure has significant impact on patient (sterility, life sustaining)

The purpose of this question is to evaluate the process/product in terms of patient risk due to potential failure of the product. Use the scoring provided. The potential for creation of critical defects in a process does not necessarily translate to a score of 9. Defects must create a significant patient risk to be scored a 9.

The potential sources of data include the Design History File (Design Control Input/Output Matrix, Product Risk Assessment, Clinical Evaluation/Studies), Risk Management File (Risk Assessment), and Classification of Defects.

The next question (Question #2) is "What is the level of regulatory risk related to this product or process?". This question is scored as follows:
Scoring:
FDA (U.S. Food and Drug Administration) Device Classifications:
1=class I device
3=class II device where process does not include labeling functions
7=class II with labeling
9=class III
EU (European Union) Device Classifications (for MD&D):
1=class I device Sterile & Non-Sterile
3=class II a device
7=class II b device
9=class III
EU (European Union) Classifications (for In-Vitro Diagnostics)*:
1=Non-Medical Device
3=Annex III (Non-Annex II)
7=Annex II List B
9=Annex II List A
*Ref: In Vitro Diagnostic Medical Devices 98/79/EC of the European Parliament & of the Council 27—October 1998

The purpose of this question is to evaluate the product/process in terms of regulatory risk using the scoring provided. If product is marketed in the European Union Countries and the United States, then the more stringent classification is selected. However, only one score (classification) can be selected. If the evaluator determines that the regulatory risk score is less than the patient risk score, then the patient risk score must be used in place of the original regulatory risk score. It should be noted that for the FDA device classifications, labeling is defined to mean final product labeling (this does not include temporary in-process component labeling, for example device lot numbers) is applied during the process being evaluated, resulting in a potential for mixes or misbranding. The potential sources of data include the Technical File/Design Dossier, the 510K, and the PMA.

The third question (Question #3) is "Are product CTQs identified and linked to VOC?". This question is scored as follows:
Scoring:
1=all, utilizing QFD or equivalent
5=some known through complaint or other history
9=none or unknown The purpose of this question is to evaluate if the CTQs (product level) are identified and linked to a formal Voice of the Customer input. For a process that has been in place for more than 4 years, CTQs can be defined as the list of defects and their defect classifications. It should be duly noted in the comments section of the scorecard if CTQ's are defined in this manner. For processes that have not been in place for more than 4 years, CTQs must be derived from a formal QFD or VOC process. This can typically be found in the original development DHF (design history file) for the device. The potential sources of data include Product Specifications/Quality Plan, QFD, Complaint history, and DHF.

The next question (Question #4) to be asked and evaluated is "Is a product risk assessment complete and risk mitigation plan in place?". This question is scored as follows:
Scoring:
1=yes
5=complete, but not all failure modes addressed
9=no or unknown The purpose of this question is to evaluate the level of completeness of the product risk assessment. The potential sources of date include the Product Risk Management File, and or FMEA.

The next question (Question #5) is "Have CTQs flowed down to component/RM (Raw Material) level with control plans in place for each component/RM?". Question # 5 is scored as follows:
Scoring:
1=all
5=some
9=none The purpose of this question is to evaluate the product/process on flow down of CTQs to the component/raw material level. Raw materials may come from an external or an internal supplier. In these cases, a control plan must exist at the supplier. The potential sources of data include the Quality Plan/Raw Material Specifications.

The sixth question (question #6) is "Do sampling plans/control strategies utilize documented statistical rationales?". This question is scored as follows:
Scoring:
1=all
7=some
9=none The purpose of this question is to evaluate whether a proper statistical rationale is utilized, in the form of a documented memo/report that directly addresses the process capability and severity of potential defects when determining the appropriate sample size, as well as any rules such as skip lots, tightened/reduced sampling, etc. For the purposes of this item, only listing a reference to the AQL/LQ of the plan is not considered adequate, and would result in a score of 7. The potential sources of data include a Six Sigma Black Belt Project/Operator Inspection Sheet/Validation/Specific Defect Audit/Incoming Inspection Sampling The next question (Question #7) that is asked is "Does a control plan exist and identify KPIVs and controls for each CTQ?". This question is scored as follows:

Scoring:
1=control plan complete and Y=f(x) relationship documented
5=some
9=no

The purpose of this question is to evaluate the product/process on adequacy of process control plans. A control plan is not an SPC control chart nor is it simply a process specification. A control plan should identify the process outputs (CTQs), measurement system, process inputs and relationship to outputs, control of inputs or monitoring of outputs, and reaction plan. If some of these elements are found in other documents, use a score of 5. The potential sources of data include Specifications/Quality Plan/Operator Inspection System.

The eighth question (Question #8) is "Is an adequate test method control identified for each CTQ?" The question is scored as follows:
Scoring:
1=GR&R<20
3=GR&R of 20-30, attribute, compendial or TM validated using other statistical TMV technique
9=GR&R>30 or unknown value or TM does not correlate to the targeted CTQ.

The purpose of this question is to evaluate the process and determine if an adequate detection system exists for each CTQ. If there are multiple test methods, the answer to this question is based on the worst-case result. By definition, "Visual Inspection" is a score of 3. Compendia) methods are also scored a 3. The scoring given refers to the Precision to Tolerance of the test method. If the TM was successfully validated using COV, % PT or any other statistical technique, then a score of 3 is selected. The potential sources of data include the Quality Plan/Test Method Validation Index.

The next question (Question #9) asked is "What is the critical defect (3 month average) process capability in DPM or Ppk (complete roll-up)?" The scoring is as follows:
Scoring:
1=less than 3.4 DPM or Ppk better than 1.5
3=Ppk 1.17 to 1.5 or DPM 233 to 3.4
9=Ppk less than 1.17 or DPM greater than 233 or unknown or no SPC The definition of a critical defect is a nonconformance to specifications, label claims, regulatory, customer or other requirements that could cause serious injury or illness to the customer. A serious injury or illness is an injury or illness that is life threatening, even if temporary in nature; results in permanent impairment of a body function or permanent damage to a body structure; or necessitates medical or surgical intervention to preclude permanent impairment of a body function or permanent damage to a body structure.

The purpose of this question is to provide a measure related to critical defects only produced in a manufacturing process. All critical defects are counted, including those detected by validated detection systems and those detected outside these validated detection points (i.e., Near Misses). This information may be provided in either DPM (defects per million units) or Ppk.

The DPM Calculation should be a cumulative and complete roll-up of the entire process as it relates to the rates of creation of these defects. Use the monthly cumulative number of all critical defects from your defect tracking system and divide by the number of units produced that month. Multiply by one million to calculate DPM. Use a 3-month average for scoring.

Ppk may substitute for DPM, if available. If the process has multiple CTQs, all defects are utilized in the calculation. The actual Ppk or DPM is documented in the comments section of the scorecard. The potential sources of data include the DPM Tracking System, Defect Tracking System (DTS) or CAPA System.

The tenth question (Question #10) asked is "Is there an Effective Training Plan defined, followed, and up to date?". This question is scored as follows:
Scoring:
1=yes
7=some
9=no The purpose of this question is training pertains to all associates who have an impact on the relevant processes, designs and opportunities to create, identify or respond to defects. "All associates" includes, but is not limited to, associates specific to the process being evaluated, in the following areas: wage, production, facilitators, engineers, quality engineers. An "effective" training plan includes some method of assuring that the training has been understood and retained (e.g., Testing, certification, etc). The potential sources of data include Personnel Training Records, Annual Assessments of Competence, and Training Plans.

The next question (Question #11) is "Are manufacturing methods and other procedures properly executed (# of process deviations)?". The question is scored as follows:
Scoring:
1=0 process deviations
3=1-2 process deviations
9=≧3 process deviations The definition of Process Deviation is the unintentional non-fulfillment of a specified requirement of a procedure regarding products, product-related processes, and quality systems.

The purpose of this question is to evaluate the process/product for unintentional process deviations per lot (unit). A minimum of a 3-month total should be provided for scoring. This should be documented in the comments section of the scorecard.

The potential sources of data include Deviation System Records, and the CAPA System The final question (Question #12) is "Is a process FMEA complete and adequate?". This question is scored as follows:
Scoring:
1=yes with acceptable RPNs
3=complete with unacceptable RPNs
9=no FMEA The purpose of this question is to assess the completeness and thoroughness of the process FMEA. The scoring provided should be used. Local process FMEA procedures should be referred to. If an RPN was considered unacceptable (unresolved) but a corrective action was put in place, choose a score of 1 and update the pFMEA. The potential sources of data include Risk Management File, Design History File, and pFMEA.

Once the questions are answered, the algorithm is used to score the results. The algorithm is PI=Severity*Detection*Occurrence divided by the maximum (23328) times 100. Severity is the sum of Questions 1 and 2. Occurrence is the sum of Questions 3, 4, 5, 7, 9, 10, 11 and 12. And, Detection is the sum of Questions 6 and 8. The PI score is then utilized to prioritize potential areas of risk in manufacturing so that quality improvement efforts can be addressed in the appropriate priority order. In order to determine the appropriate alert level (threshold) for determining which potential risks require corrective action plans, the PI tool should be utilized to score example manufacturing processes that have and have not had historical quality problems. An appropriate number of processes of each type should be scored using the tool. An analysis using appropriate statistical techniques should then be utilized to analyze the results and determine the cut-off point between the high and low risk processes. As an example, an alert level of 45 was calculated for a particular business by scoring processes, creating box plots of processes which generated product involved with product recalls, and processes producing product with no recall events. By evaluating the box plots, an appropriate alert level was derived for the business.

Although this invention has been shown and described with respect to detailed embodiments thereof, it will be understood by those skilled in the art that various changes in form and detail thereof may be made without departing from the spirit and scope of the claimed invention.

We claim:

1. A method for manufacturing an improved medical device, comprising:
   providing a suitably programmed computer for calculating a risk score associated with the manufacturing process;
   executing upon the suitably programmed computer a predictive indicator tool for analyzing the manufacturing process to determine each sub-process, the predictive indicator tool for each manufacturing sub-process including:
   A. 1) inputting the Level of Patient Risk due to potential failure of the medical device,
   2) inputting the Level of Regulatory Risk related to the medical device,
   3) inputting data related to whether product CTQs are identified and linked to VOC,
   4) inputting data related to whether a Product Risk Assessment is complete and a risk mitigation plan is in place,
   5) inputting data related to whether CTQs have flowed down to component/RM level with control plans in place for each component/RM,
   6) inputting data related to whether Sampling Plans/Control strategies utilize documented statistical rationales,
   7) inputting data related to whether a Control Plan Exists and identify KPIVs and controls for each CTQ,
   8) inputting data related to whether an Adequate Test Method control is identified for each CTQ,
   9) inputting data related to Critical Defect (3 month average) Process Capability in DPM or PpK (complete roll-up),
   10) inputting data related to whether there is an Effective Training Plan defined, followed, and up to date,
   11) inputting data related to whether manufacturing Methods and other procedures are properly executed (# of human error deviations),
   12) inputting data related to whether Process FMEA is complete and adequate,
   B. scoring the data inputted for each of the twelve data input areas and determining a risk score for the process by using the following algorithm:

$$PI = Severity * Detection * Occurrence / 23328 * 100,$$
   wherein
   Severity=the sum of the scores of Questions 1 and 2,
   Occurrence=the sum of the scores of Questions 3, 4, 5, 7, 9, 10, 11, 12
   Detection=the sum of the scores of Questions 6 and 8; and
   C. outputting the risk score to the user.

2. The method of claim 1, comprising the additional step of ranking and prioritizing the sub processes.

3. The method of claim 2, additionally comprising the step of developing a mitigation plan to decrease the risk score.

* * * * *